United States Patent
Ong et al.

(10) Patent No.: US 10,717,689 B2
(45) Date of Patent: Jul. 21, 2020

(54) ENHANCING THERMAL STABILITY OF BULK HETEROJUNCTION SOLAR CELLS WITH FLUORENONE DERIVATIVES

(71) Applicant: Hong Kong Baptist University, Hong Kong (HK)

(72) Inventors: Beng Soon Ong, Toronto (CA); Yong Lu, Hong Kong (HK); Carr Hoi Yi Ho, Hong Kong (HK); Huanyang Cao, Hong Kong (HK); Sin Hang Cheung, Hong Kong (HK); Ka Lok Chiu, Hong Kong (HK); Shu Kong So, Hong Kong (HK)

(73) Assignee: Hong Kong Baptist University, Hong Kong (CN)

( * ) Notice: Subject to any disclaimer, the term of this patent is extended or adjusted under 35 U.S.C. 154(b) by 165 days.

(21) Appl. No.: 15/688,881

(22) Filed: Aug. 29, 2017

(65) Prior Publication Data
US 2018/0057428 A1    Mar. 1, 2018

Related U.S. Application Data

(60) Provisional application No. 62/381,091, filed on Aug. 30, 2016.

(51) Int. Cl.
| | |
|---|---|
| *C07C 13/567* | (2006.01) |
| *H01L 51/00* | (2006.01) |
| *C07C 255/41* | (2006.01) |
| *H01L 51/42* | (2006.01) |

(52) U.S. Cl.
CPC .......... *C07C 13/567* (2013.01); *C07C 255/41* (2013.01); *H01L 51/0052* (2013.01); *C07C 2603/18* (2017.05); *H01L 51/4253* (2013.01); *Y02E 10/549* (2013.01)

(58) Field of Classification Search
CPC ............ H01L 51/0052; H01L 51/4253; Y02E 10/549; C07C 255/41; C07C 13/567; C07C 2506/18
See application file for complete search history.

(56) References Cited

U.S. PATENT DOCUMENTS

| | | | | |
|---|---|---|---|---|
| 2010/0294368 | A1* | 11/2010 | Ushiro | ............... H01L 51/4226 136/263 |
| 2011/0210315 | A1* | 9/2011 | Goel | ................. C07D 207/327 257/40 |
| 2012/0042923 | A1* | 2/2012 | Tsai | ................. H01L 31/02021 136/244 |

FOREIGN PATENT DOCUMENTS

WO    WO-2005078742 A2 *    8/2005    ............. H01B 1/127

* cited by examiner

*Primary Examiner* — Uyen M Tran
(74) *Attorney, Agent, or Firm* — Spruson & Ferguson (Hong Kong) Limited

(57) ABSTRACT

The present invention relates to the provision of an organic compound or compounds containing a fluorenone derivative structure or its substituted derivatives to enhance the thermal stability of organic solar cells.

3 Claims, 2 Drawing Sheets

ENHANCING THERMAL STABILITY OF BULK HETEROJUNCTION SOLAR CELLS WITH FLUORENONE DERIVATIVES

CROSS-REFERENCE TO RELATED APPLICATIONS

This application claims priority from U.S. Provisional Patent Application Ser. No. 62/381,091 filed on Aug. 30, 2016, the disclosure of which is hereby incorporated by reference.

FIELD OF THE INVENTION

The present invention relates to the provision of an organic compound or compounds containing a fluorenone derivative structure or its substituted derivatives to enhance the thermal stability of organic solar cells.

BACKGROUND OF THE INVENTION

Owing to the concerns over diminishing fossil fuels and severe environmental damages caused by emissions from conversion of fossil fuel to energy, renewable clean energy has become a topic of immense interest and pressing urgency. In recent years, harvesting solar energy has received growing attention as a feasible renewable green energy solution. This may be competitive with other renewable energies such as hydro and wind powers if the efficiency of harvesting devices can be optimized and their associated implementation costs minimized. Today, solar energy conversion to electricity using silicon-based solar panels remains one of the costliest green energy approaches, despite recent plummets in solar panel costs by as much as 70%. Accordingly, the potential of using organic solar cells to reduce costs has emerged since solar cells made from organic materials may be significantly cheaper and their installation, less cost-intensive, enabling substantially reduced total costs of solar energy conversion.

One of the most studied organic solar cells is bulk heterojunction organic solar cells (BHJ-OSCs), which utilize an active layer composed of an organic electron donor and acceptor dispersion in which the donor and acceptor domain sizes are on the order of nanometers. These nanoscale domains form continuous percolated pathways for the transport of charge carriers (holes and electrons) following their dissociation from excitons after photoexcitation.

Light absorption occurs in the electron donor or acceptor domains or both, resulting in the formation of excitons, which travel to the electron donor/acceptor domain interfaces and dissociate into charge carriers. Thus, the efficiency of BHJ-OSCs is critically dependent on the efficacies of light absorption, exciton formation and dissociation as well as the transport of dissociated electrons and holes to the cathode and anode, respectively.

Presently, the most utilized acceptor material for BHJ-OSCs is fullerene derivatives (hereinafter referred to as PCBM) such as [6,6]-phenyl-C61-butyric acid methyl ester (PC60BM) or [6,6]-phenyl-C71-butyric acid methyl ester (PC70BM), while the donor compounds are primarily p-type conjugated polymers such as P3HT, PTB7, PffBT4T-2OD, etc. For efficient energy conversion, the percolated nanoscale dispersion morphology of the donor and acceptor materials in the active layer, which promotes rapid transport of electrons and holes to their respective electrodes, is essential.

To ensure effective dispersion of PCBM acceptor and donor polymer to form proper nanoscale domain morphology for efficient carrier transport, suitable processing additives such as 1,8-diiodooctane (DIO) or 1,8-octanediitol and the like are often added in the coating solution during solution deposition of the active layer.

The results show that the processing additive such as DIO greatly enhances nanoscale dispersion formation, leading to higher power conversion efficiency (PCE) of the resulting solar cells. However, it has been found that the nanoscale dispersions in the active layer are sensitive to their thermal environment, and morphology changes or degradation arising from thermally induced aggregation of nanoscale domains occurs as the temperature rises above room temperature. These changes have led to disruption of percolated charge transport pathways, resulting in significantly degraded PCEs.

This is particularly worrisome as the solar cells, during normal operation under direct sunlight irradiation, would be subject to temperatures significantly higher than room temperature (e.g. up to 60° C.). Thus, the performance degradation of OSCs as a result of sunlight exposure would limit their potential utility, severely hampering their practical adoption in mainstream applications. Accordingly, for practical utility of fullerene-based BHJ-OSCs, it is imperative that the thermal stability of the active layer be significantly improved in order to sustain the PCE of solar cells.

It is thus an objective of the present invention to provide an organic compound or compounds containing a fluorenone derivative structure to enhance the thermal stability of organic solar cells.

Another objective of the present invention is the provision of an active layer composition for organic solar cells wherein said composition comprises a PCBM acceptor, a donor polymer, optional processing additives, and a fluorenone derivative such that the resulting solar cells possess enhanced thermal stability.

A further objective of the present invention is to provide an organic BHJ-OSC with greatly enhanced thermal stability, and wherein its active layer composition contains a fluorenone derivative.

Citation or identification of any reference in this section or any other section of this application shall not be construed as an admission that such reference is available as prior art for the present application.

SUMMARY OF THE INVENTION

Accordingly, the objective of this invention relates in general to organic solar cells containing a fluorenone derivative which enhances the thermal stability of organic solar cells. The enhancement in thermal stability may be related, but not limited to, facilitation of processing of active layer fabrication and subsequent stabilization of the nanoscale morphology of the active layer by the fluorenone derivative against thermally-induced degradation.

In a first aspect of the present invention, there is provided an electron deficient compound used as an additive in an active layer in an organic solar cell to enhance its photovoltaic thermal stability wherein said compound comprises at least one chemical structural unit of (I):

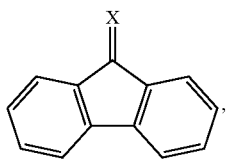

(I)

wherein X is oxygen (O) or dicyanomethylene [C(CN)$_2$].

In a first embodiment of the first aspect of the present invention, there is provided an electron deficient compound used as an additive in an active layer in an organic solar cell wherein said compound further comprises a chemical structure of (II), (III), or (IV):

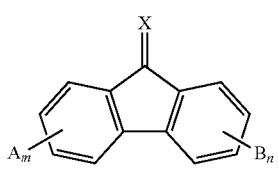

(II)

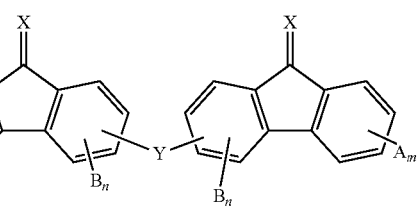

(III)

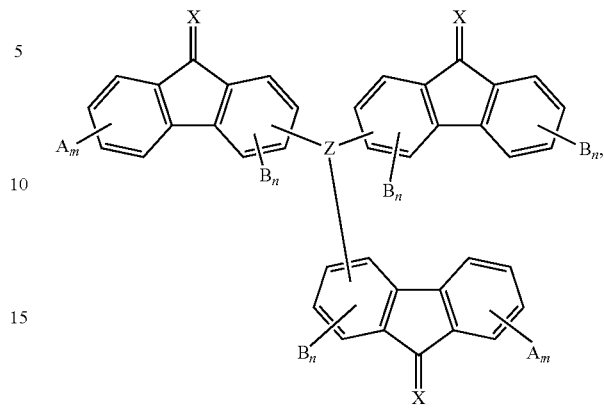

(IV)

wherein X is oxygen atom (O) or dicyanomethylene [C(CN)$_2$]; A and B are substituents jointly or separately selected from the group consisting of alkyl, alkoxy, halogen, cyano, and nitro groups; Y is a divalent linkage selected from the group consisting of methylene, dimethylene, trimethylene, substituted polymethylene [e.g., —CH$_2$CH(CH$_2$CH$_3$)CH$_2$CH(CH$_2$CH$_3$)CH$_2$—], alkylbis(polymethylene)amine [e.g., —(CH$_2$)$_2$NCH$_3$(CH$_2$)$_2$—], and other substituted polymethylene [e.g., —COOCH$_2$OOC—; —COOCH$_2$CH$_2$OOC—]; Z is a trivalent linkage selected from the group consisting of tris(polymethylene) amine [e.g., [—(CH$_2$)$_2$]$_3$N]; m and n are jointly or separately selected from an integer ranging from zero to 3.

In a second embodiment of the first aspect of the present invention, there is provided an electron deficient compound used as an additive in an active layer in an organic solar cell wherein the compound further comprises a chemical structure of (V), (VI), (VII), (XII), (XIII), or (XIV):

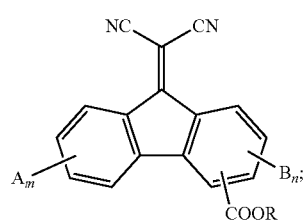

(V)

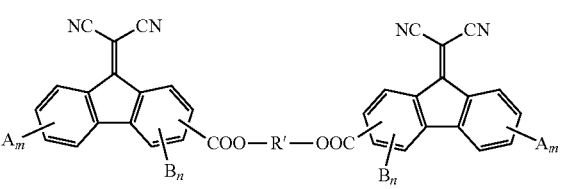

(VI)

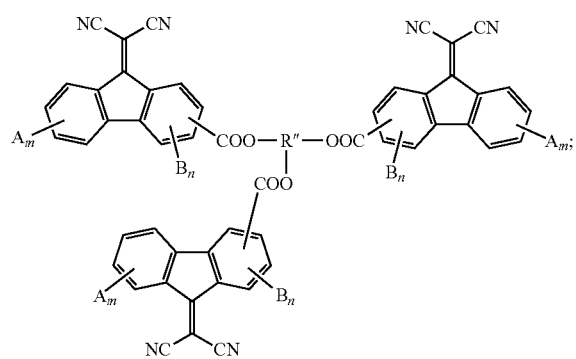

(VII)

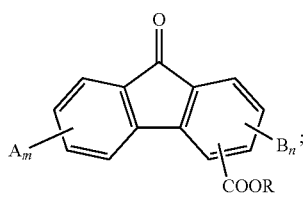

(XII)

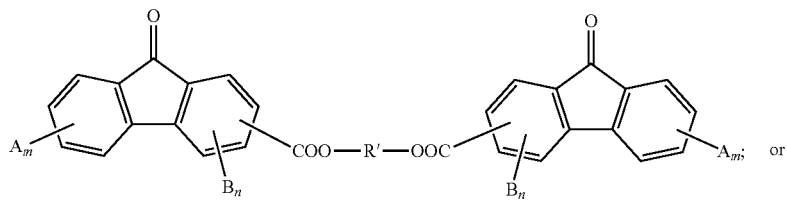
(XIII)

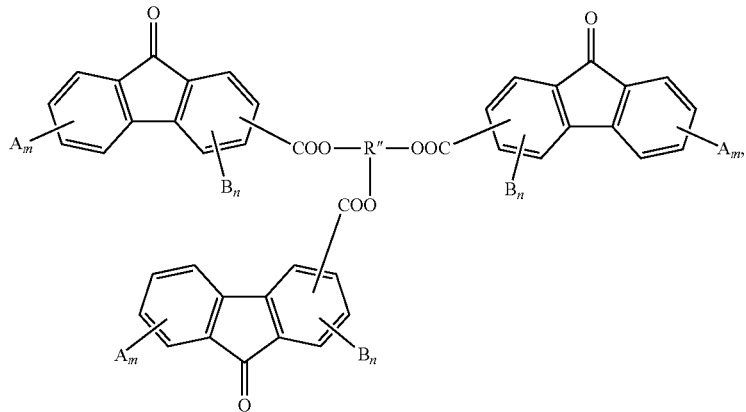
(XIV)

wherein A and B are substituents jointly or separately selected from the group consisting of alkyl, alkoxy, halogen, cyano and nitro groups; R is an alkyl group; R' is a divalent linkage selected from the group consisting of methylene, dimethylene, trimethylene, substituted polymethylene [e.g., —$CH_2CH(CH_2CH_3)CH_2CH(CH_2CH_3)CH_2$—], alkylbis(polymethylene)amine [e.g., —$(CH_2)_2NCH_3(CH_2)_2$—], their substituted forms and analogs; R" is a trivalent linkage such as tris(polymethylene) amine [e.g., [—$(CH_2)_2]_3N$]; m and n are jointly or separately selected from an integer ranging from zero to 3.

In a third embodiment of the first aspect of the present invention, there is provided an electron deficient compound used as an additive in an active layer in an organic solar cell wherein the compound further comprises a chemical structure of:

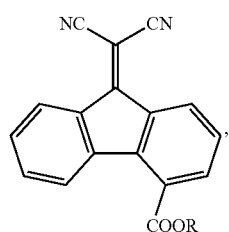

wherein R is —$(CH_2)_3CH_3$, —$(CH_2)_7CH_3$, —$(CH_2)_3CH(CH_3)_2$, or —$(CH_2)_3CH(CH_3)CH_2CH_3$;

or

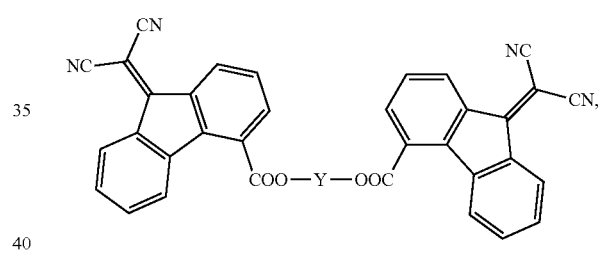

wherein Y is —$(CH_2)_6$—, —$(CH_2)_2NCH_3(CH_2)_2$—, —$CH_2CH(CH_3)CH_2CH(CH_3)CH_2$—, —$CH_2CH(CH_2CH_3)CH_2CH(CH_2CH_3)CH_2$—, or —$(CH_2)_2C(CH_3)_2CH_2CH_2C(CH_3)_2(CH_2)_2$—;

or

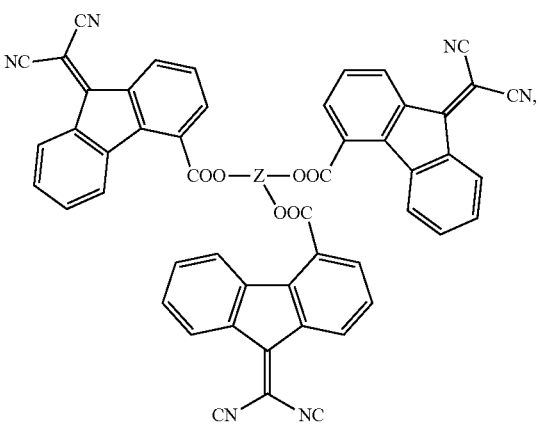

wherein Z is (—$CH_2CH_2)_3N$, (—$CH_2CH_2)_3CCH_2CH_3$, or (—$CH_2CH_2CH_2)_3CH$.

In a fourth embodiment of the first aspect of the present invention, there is provided an electron deficient compound used as an additive in an active layer in an organic solar cell wherein the compound is represented by a chemical structure of (VIII), (IX), (X), (XI), (XV), (XVI), (XVII), or (XVIII):

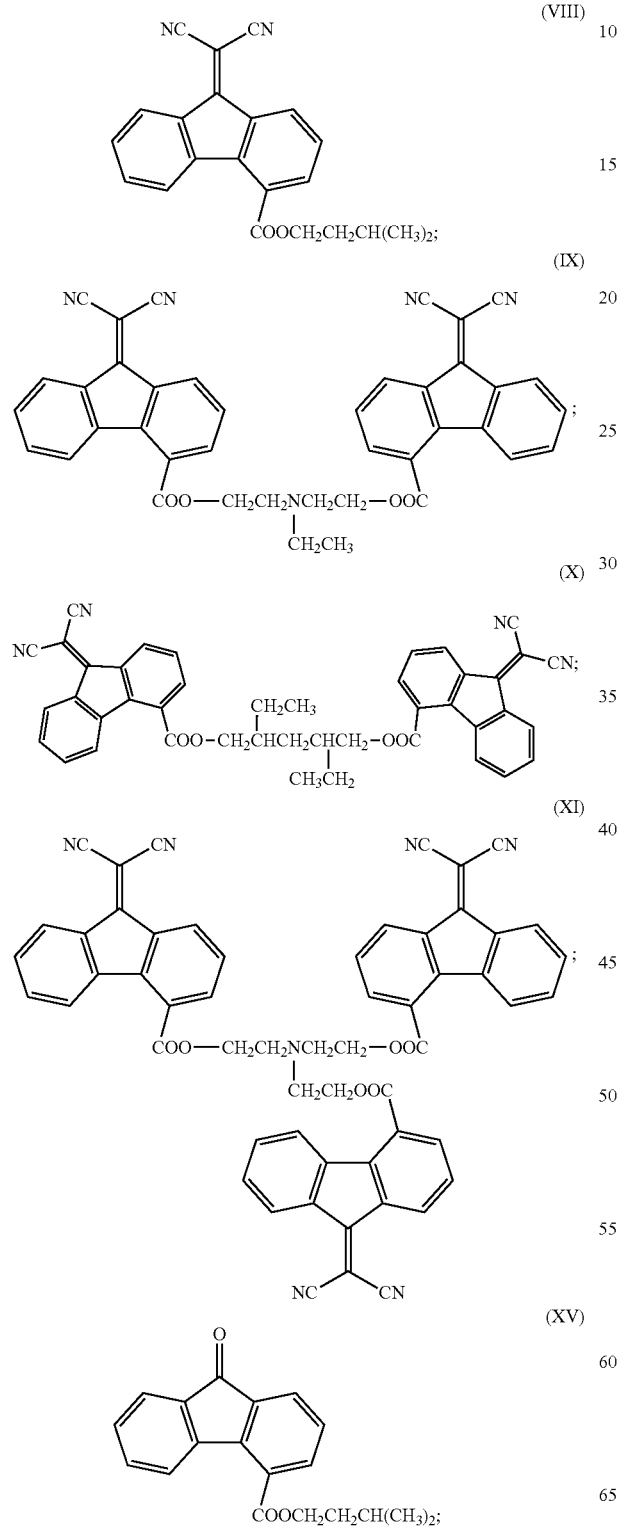

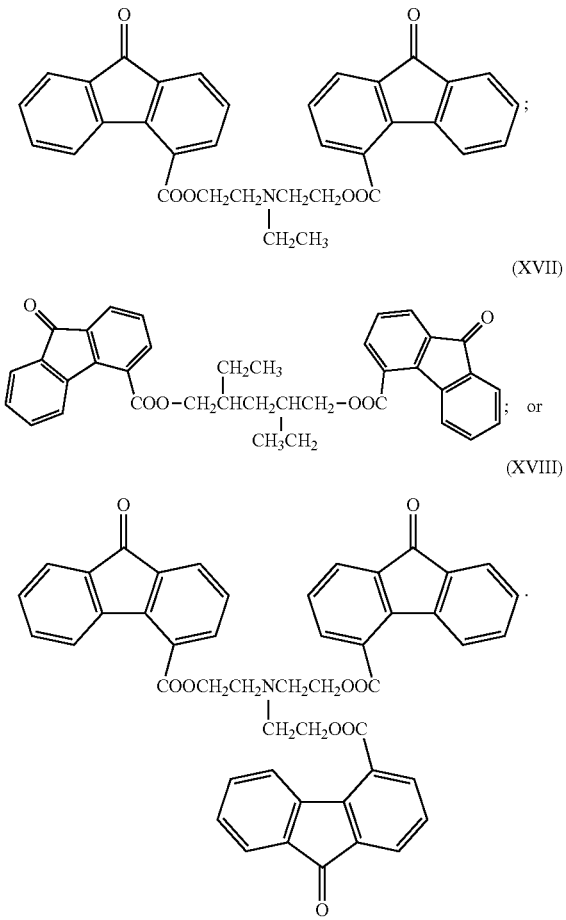

In a second aspect of the present invention, there is provided a method of forming at least one active layer in an organic solar cell comprising using the compound as described in the first aspect, which comprises a structure of (I), (II), (III), (IV), (V), (VI), (VII), (XII), (XIII), (XIV), (VIII), (IX), (X), (XI), (XV), (XVI), (XVII), or (XVIII) in an amount ranging from about 0.01 to 5 percent by weight relative to the weight of the donor polymer of the active layer of the organic solar cell.

In a first embodiment of the second aspect of the present invention, there is provided a method of forming at least one active layer in an organic solar cell comprising using the compound which comprises a structure of (I), (II), (III), (IV), (V), (VI), (VII), (XII), (XIII), (XIV), (VIII), (IX), (X), (XI), (XV), (XVI), (XVII), or (XVIII) wherein said at least one active layer is sandwiched between a cathode and an anode.

In a third aspect of the present invention, there is provided an organic solar cell having at least one active layer comprising a PCBM acceptor, a donor polymer and the compound which comprises a structure of (I), (II), (III), (IV), (V), (VI), (VII), (XII), (XIII), (XIV), (VIII), (IX), (X), (XI), (XV), (XVI), (XVII), or (XVIII).

In a fourth aspect of the present invention, there is provided an organic solar cell having an active layer comprising an electron deficient compound used as an additive, a donor polymer, and a PCBM acceptor, wherein said compound comprises at least one chemical structural unit of (I):

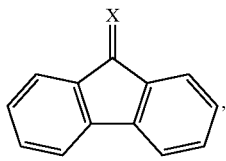

wherein X is oxygen (O) or dicyanomethylene [C(CN)$_2$].

In a first embodiment of the fourth aspect of the present invention, said compound further comprises a chemical structure of (II), (III), or (IV):

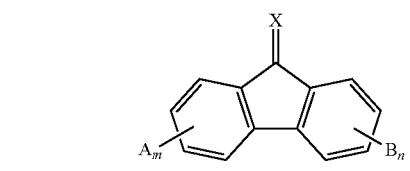

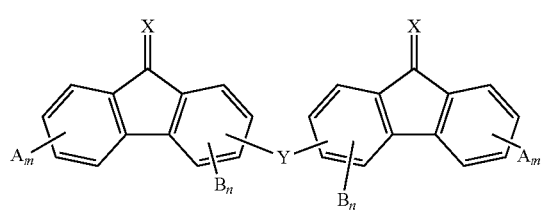

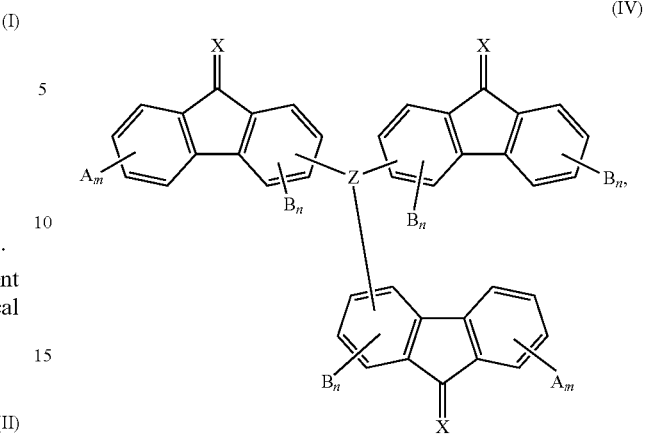

wherein X is oxygen atom (O) or dicyanomethylene [C(CN)$_2$]; A and B are substituents jointly or separately selected from the group consisting of alkyl, alkoxy, halogen, cyano, and nitro groups; Y is a divalent linkage selected from the group consisting of methylene, dimethylene, trimethylene, substituted polymethylene [e.g., —CH$_2$CH(CH$_2$CH$_3$)CH$_2$CH(CH$_2$CH$_3$)CH$_2$—], alkylbis(polymethylene)amine [e.g., —(CH$_2$)$_2$NCH$_3$(CH$_2$)$_2$—], and other substituted polymethylene [e.g., —COOCH$_2$OOC—; —COOCH$_2$CH$_2$OOC—]; Z is a trivalent linkage selected from the group consisting of tris(polymethylene) amine [e.g., [—(CH$_2$)$_2$]$_3$N]; m and n are jointly or separately selected from an integer ranging from zero to 3.

In a second embodiment of the fourth aspect of the present invention, said compound further comprises a chemical structure of (V), (VI), (VII), (XII), (XIII), or (XIV):

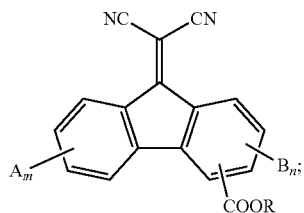

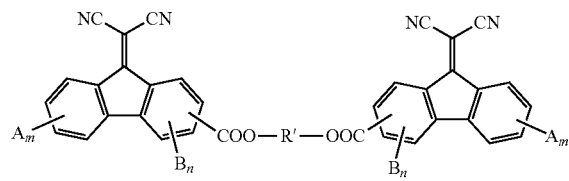

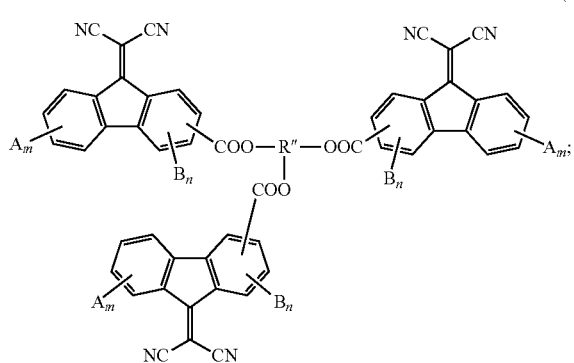

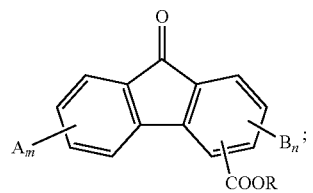

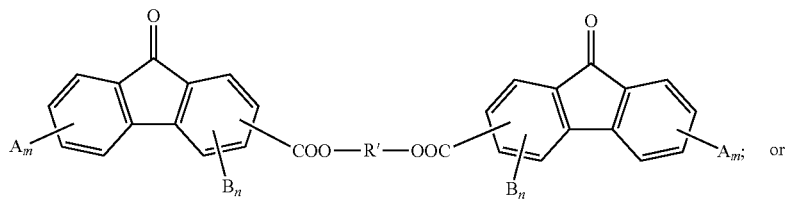

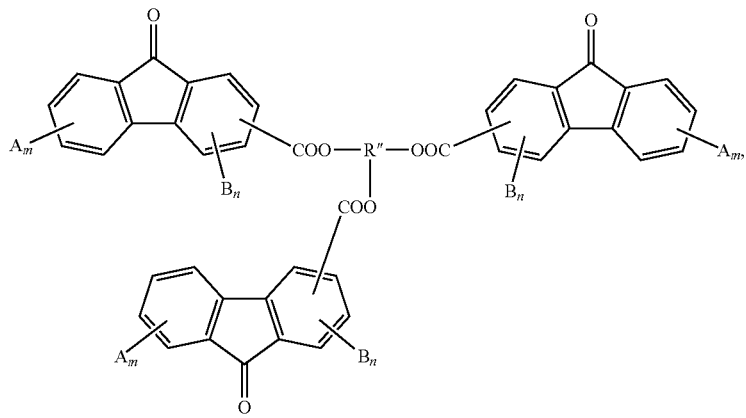

wherein A and B are substituents jointly or separately selected from the group consisting of alkyl, alkoxy, halogen, cyano and nitro groups; R is an alkyl group; R' is a divalent linkage selected from the group consisting of methylene, dimethylene, trimethylene, substituted polymethylene [e.g., —CH$_2$CH(CH$_2$CH$_3$)CH$_2$CH(CH$_2$CH$_3$)CH$_2$—], alkylbis(polymethylene)amine [e.g., —(CH$_2$)$_2$NCH$_3$(CH$_2$)$_2$—], their substituted forms and analogs; R" is a trivalent linkage such as tris(polymethylene) amine [e.g., [—(CH$_2$)$_2$]$_3$N]; m and n are jointly or separately selected from an integer ranging from zero to 3.

In a third embodiment of the fourth aspect of the present invention, said compound further comprises a chemical structure of:

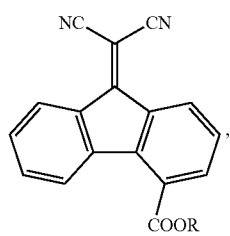

wherein R is —(CH$_2$)$_3$CH$_3$, —(CH$_2$)$_7$CH$_3$, —(CH$_2$)$_3$CH(CH$_3$)$_2$, or —(CH$_2$)$_3$CH(CH$_3$)CH$_2$CH$_3$;

or

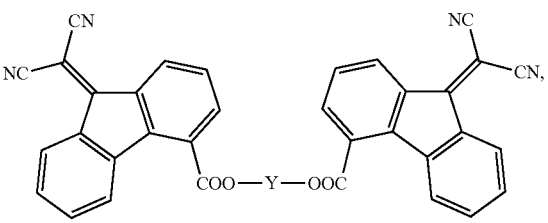

wherein Y is —(CH$_2$)$_6$—, —(CH$_2$)$_2$NCH$_3$(CH$_2$)$_2$—, —CH$_2$CH(CH$_3$)CH$_2$CH(CH$_3$)CH$_2$—, —CH$_2$CH(CH$_2$CH$_3$)CH$_2$CH(CH$_2$CH$_3$)CH$_2$—, or —(CH$_2$)$_2$C(CH$_3$)$_2$CH$_2$CH$_2$C(CH$_3$)$_2$(CH$_2$)$_2$—;

or

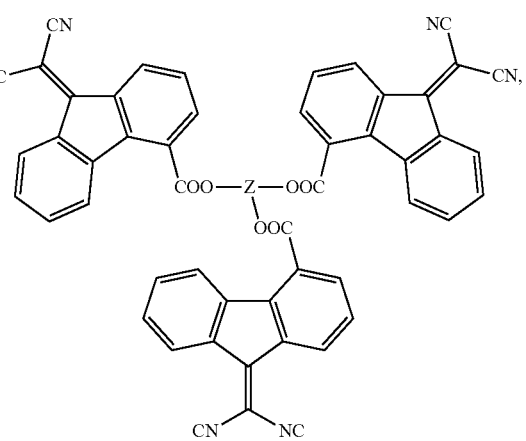

wherein Z is (—CH$_2$CH$_2$)$_3$N, (—CH$_2$CH$_2$)$_3$CCH$_2$CH$_3$, or (—CH$_2$CH$_2$CH$_2$)$_3$CH.

In a fourth embodiment of the fourth aspect of the present invention, said compound is represented by a chemical structure of (VIII), (IX), (X), (XI), (XV), (XVI), (XVII), or (XVIII):

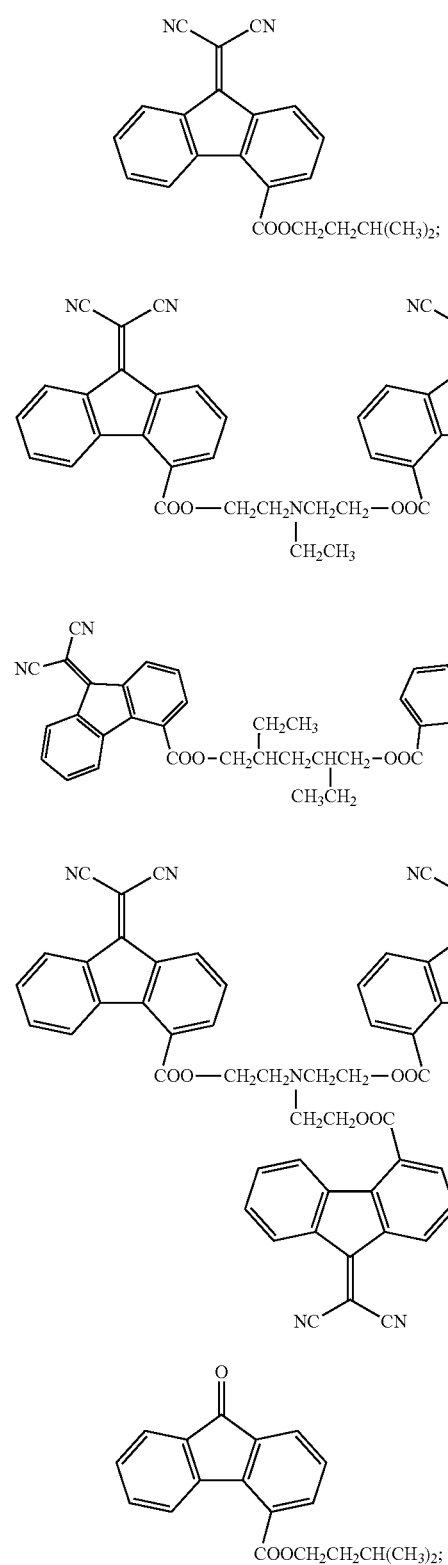

In a fifth embodiment of the fourth aspect of the present invention, said compound is present in an amount ranging from about 0.01 to 5 percent in weight relative to the weight of the donor polymer of the active layer of the organic solar cell.

In a sixth embodiment of the fourth aspect of the present invention, the compound is from 0.1 to 2% by weight to the weight of the donor polymer of the at least one active layer of the organic solar cell.

In a seventh embodiment of the fourth aspect of the present invention, one or more of processing additives are optionally added into the at least one active layer of the organic solar cell, which include but not limited to 1,8-diiodooctane (DIO) and 1,8-octaneditiol. The one or more processing additives is/are added in a range from 0.5 to 5% by volume to the total volume of a composition for forming the at least one active layer, where said composition further comprises an organic solvent to dissolve a PCBM acceptor, a donor polymer, the compound of the first aspect of the present invention. Said organic solvent includes but not limited to chlorobenzene (CB) or dichlorobenzene (DCB).

In an eighth embodiment of the fourth aspect of the present invention, said donor polymer comprises one or more of p-type conjugated polymers such as P3HT, PTB7, and PffBT4T-2OD.

In a ninth embodiment of the fourth aspect of the present invention, said PCBM acceptor comprises [6,6]-phenyl- C61-butyric acid methyl ester (PC60BM) or [6,6]-phenyl-C71-butyric acid methyl ester (PC70BM).

In a tenth embodiment of the fourth aspect of the present invention, said active layer is sandwiched between at least one anode and one cathode in order to form said organic solar cell.

In an eleventh embodiment of the fourth aspect of the present invention, said anode is aluminum (Al) based with optional hole and electron transport interlayers.

In a twelfth embodiment of the fourth aspect of the present invention, said cathode is indium tin oxide (ITO) based with optional hole and electron transport interlayers.

In a thirteenth embodiment of the fourth aspect of the present invention, said at least one anode and one cathode are Al based and ITO based, respectively, with optional hole and electron transport interlayers comprising LiF and PEDOT:PSS such that said anode is LiF/Al and said cathode is ITO/PEDOT:PSS, respectively.

Those skilled in the art will appreciate that the invention described herein is susceptible to variations and modifications other than those specifically described.

The invention includes all such variation and modifications. The invention also includes all of the steps and features referred to or indicated in the specification, individually or collectively, and any and all combinations or any two or more of the steps or features.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Furthermore, throughout the specification and claims, unless the context requires otherwise, the word "include" or variations such as "includes" or "including", will be understood to imply the inclusion of a stated integer or group of integers but not the exclusion of any other integer or group of integers.

Other definitions for selected terms used herein may be found within the detailed description of the invention and apply throughout. Unless otherwise defined, all other technical terms used herein have the same meaning as commonly understood to one of ordinary skill in the art to which the invention belongs.

Other aspects and advantages of the invention will be apparent to those skilled in the art from a review of the ensuing description.

BRIEF DESCRIPTION OF DRAWINGS

The above and other objects and features of the present invention will become apparent from the following description of the invention, when taken in conjunction with the accompanying drawings, in which.

DETAILED DESCRIPTION OF THE INVENTION

The present invention is not to be limited in scope by any of the specific embodiments described herein. The following embodiments are presented for exemplification only.

Figure 1:
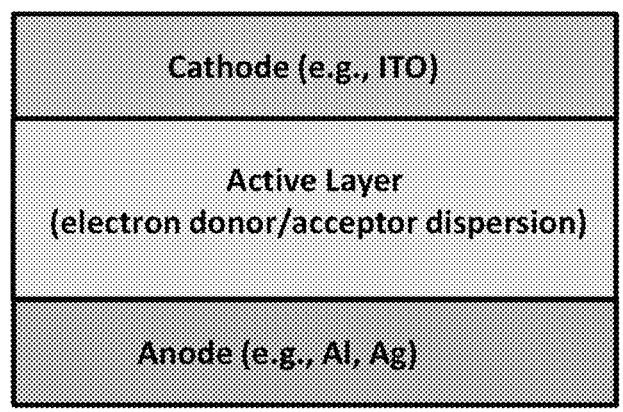
FIG. 1 shows the schematic diagram of an organic bulk heterojunction solar cell.

The present invention relates to an electron-deficient fluorenone derivative containing a chromophore structure of formula (I) or its substituted derivative, which when it is present in the composition of organic solar cells, it enhances their thermal stability. Specifically, said fluorenone derivative is present in the active layer of organic solar cells whose structure is schematically represented in FIG. 1, in which the active layer is sandwiched between two electrodes (cathode and anode). More specifically, said fluorenone derivative can be utilized in the active layer of a BHJ-OSC, whose structure is for example represented in FIG. 2, in which an active layer comprises a donor polymer, PCBM, optional processing additives, and said fluorenone derivative. Said active layer may be sandwiched in between an ITO cathode and an Al anode with optional hole and electron transport interlayers as represented for example by PEDOT:PSS and LiF, respectively, to promote and facilitate charge carrier injection and transport. Said formula (I) is as follows:

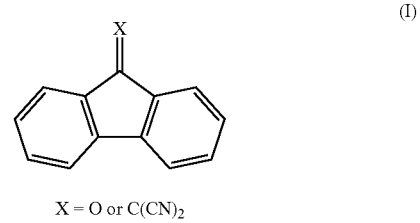

(I)

X = O or C(CN)$_2$

The said thermal stability of organic solar cells may be related, but not limited to, facilitation of processing of active layer fabrication and subsequent stabilization of the nanoscale morphology of their active layers by the fluorenone derivative against thermally-induced degradation.

The stabilization presumably arises from the charge transfer interaction between the fluorenone derivative, which is a strong electron acceptor, and the donor moiety of the donor polymer. This in essence results in physically "cross-linking" the donor polymer molecules by said fluorenone derivative, promoting and facilitating formation of donor polymer nanodomains. The physical cross-linking of the donor polymers also contributes to the isolation and stabilization of PCBM nanodomains, thus ensuring continuous percolated transport pathways for both electron and hole carriers.

Preferably, the fluorenone derivatives of the present invention, that are useful for thermal stabilization of OSCs are represented by the following general formulas:

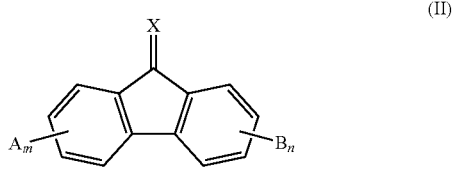

(II)

(III)

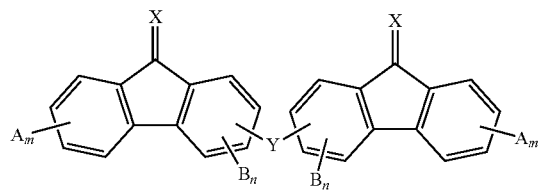

(IV)

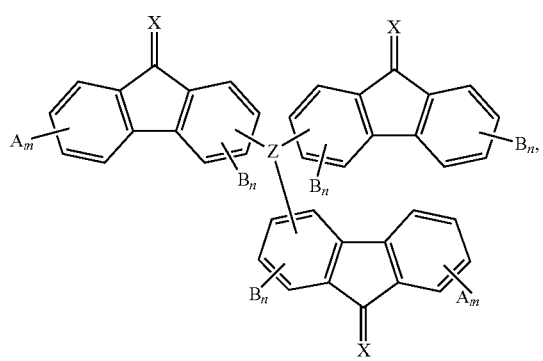

where X is oxygen atom (O) or dicyanomethylene [C(CN)₂]; A and B, jointly or separately, are substituents such as alkyl, alkoxy, halogen, cyano, nitro groups and the like; Y is a divalent linkage such as methylene, dimethylene, trimethylene, substituted polymethylene [e.g., —CH₂CH(CH₂CH₃)CH₂CH(CH₂CH₃)CH₂—], alkylbis(polymethylene)amine [e.g., —(CH₂)₂NCH₃(CH₂)₂—], other substituted polymethylene [e.g., —COOCH₂OOC—; —COOCH₂CH₂OOC—], and the like; Z is a trivalent linkage such as tris(polymethylene) amine [e.g., [—(CH₂)₂]₃N] and the like; m and n are integers ranging from zero to 3.

More specifically, the fluorenone derivatives that are of particular interest are fluorenylidene malononitrile derivatives and the like represented by the following structures:

(V)

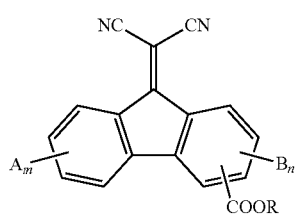

(VI)

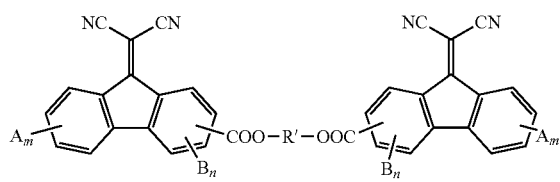

(VII)

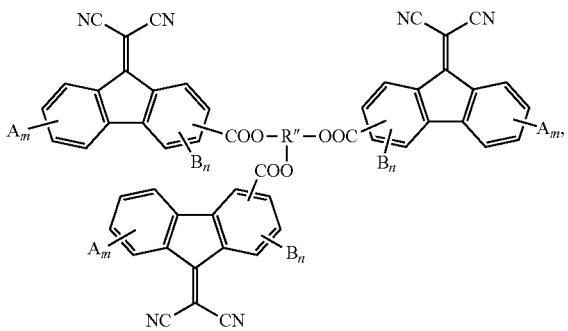

where A and B, jointly or separately, are substituents such as alkyl, alkoxy, halogen, cyano, nitro groups and the like; R is an alkyl group; R' is a divalent linkage such as methylene, dimethylene, trimethylene, substituted polymethylene [e.g., —CH₂CH(CH₂CH₃)CH₂CH(CH₂CH₃)CH₂—], alkylbis(polymethylene)amine [e.g., —(CH₂)₂NCH₃(CH₂)₂—], their substituted forms and the like; R" is a trivalent linkage such as tris(polymethylene) amine [e.g., [—(CH₂)₂]₃N] and the like; m and n, jointly or separately, are integers ranging from zero to 3.

The fluorenylidene manolonitriles that are of specific interest to the present invention include but not limited to the following compounds:

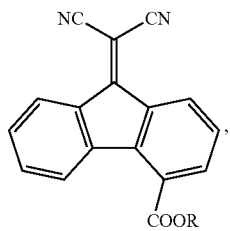

where R=—(CH₂)₃CH₃, —(CH₂)₇CH₃, —(CH₂)₃CH(CH₃)₂, —(CH₂)₃CH(CH₃)CH₂CH₃;

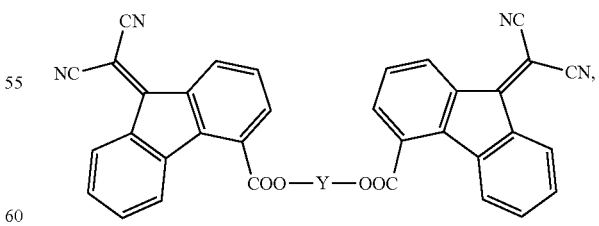

where Y=—(CH₂)₆—; —(CH₂)₂NCH₃(CH₂)₂—, —CH₂CH(CH₃)CH₂CH(CH₃)CH₂—, —CH₂CH(CH₂CH₃)CH₂CH(CH₂CH₃)CH₂—, —(CH₂)₂C(CH₃)₂CH₂CH₂C(CH₃)₂(CH₂)₂—; and

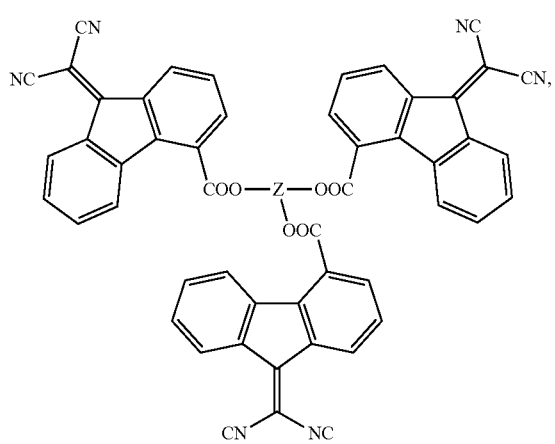

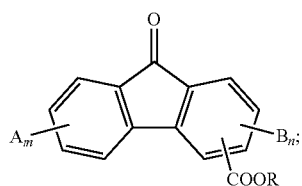

(XII)

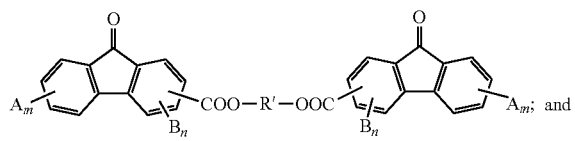

(XIII)

where Z=(—CH$_2$CH$_2$)$_3$N, (—CH$_2$CH$_2$)$_3$CCH$_2$CH$_3$, (—CH$_2$CH$_2$CH$_2$)$_3$CH.

Four illustrative specific examples of fluorenylidene malononitriles useful for the present invention are provided below:

In other embodiments of the present invention, the following illustrative fluorenone derivatives are also useful additives of the present invention:

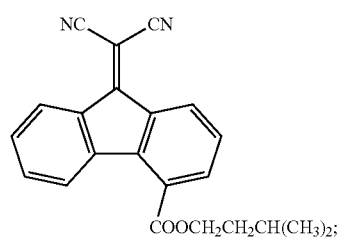

(VIII)

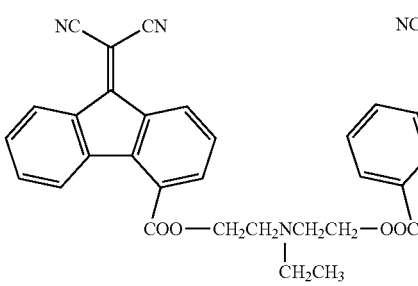

(IX)

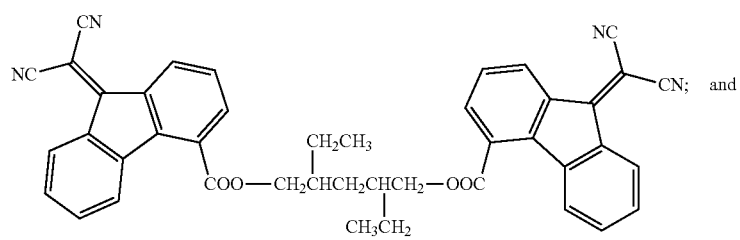

(X)

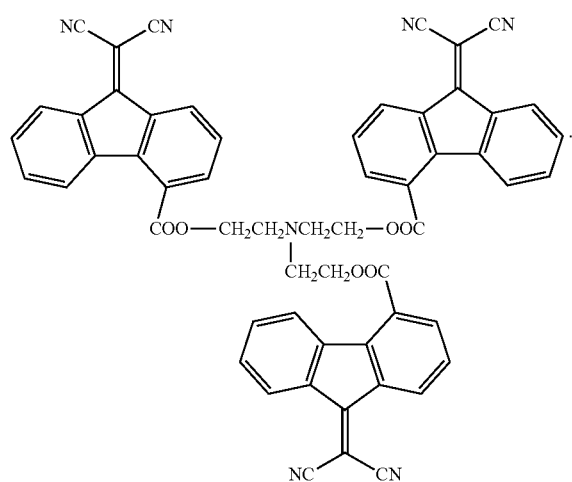

(XI)

(XIV)

Figure 2:
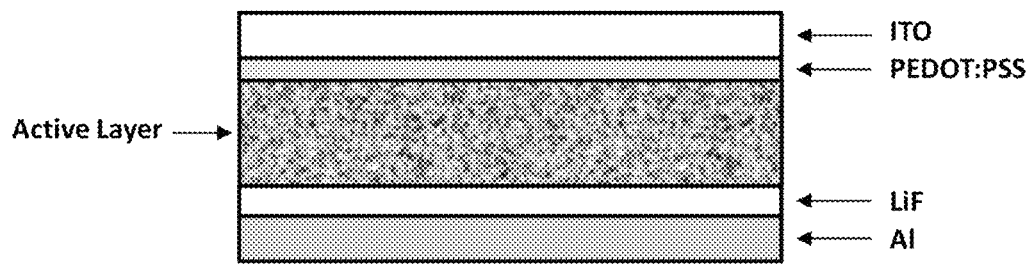
FIG. 2 shows the structural configuration of sample BHJ-OSC device.

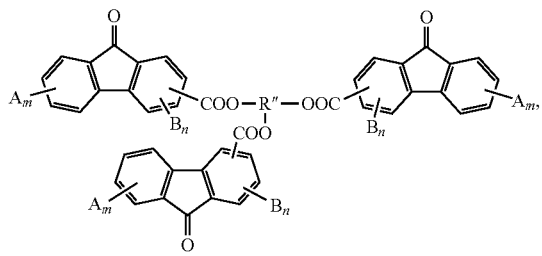

where A and B, jointly or separately, are substituents such as alkyl, alkoxy, halogen, cyano, nitro groups and the like; R is an alkyl group; R' is a divalent linkage such as methylene, dimethylene, trimethylene, substituted polymethylene [e.g., —CH$_2$CH(CH$_2$CH$_3$)CH$_2$CH(CH$_2$CH$_3$)CH$_2$—], alkylbis(polymethylene)amine [e.g., —(CH$_2$)$_2$NCH$_3$(CH$_2$)$_2$—], their substituted forms and the like; R" is a trivalent linkage such as tris(polymethylene) amine [e.g., [—(CH$_2$)$_2$]$_3$N] and the like; m and n, jointly or separately, are integers ranging from zero to 3;

PCBM, and fluorenone derivative) are first dissolved in a suitable solvent such as chlorobenzene (CB) or dichlorobenzene (DCB) together with optional processing additive such as 1,8-diiodooctane (DIO) in the amount of 0.5% to 5% by volume relative to the total volume of active layer coating solution. Illustrative device configuration of the sample BHJ-OSC device is ITO/PEDOT:PSS/active layer/LiF/Al as represented in FIG. 2.

The active layer coating solution (donor polymer/PCBM/fluorenone derivative/DIO/CB) is then spin coated onto PEDOT:PSS-coated ITO glass substrate, and dried in vacuo, followed by heating in an oven at an appropriate temperature from 10 min to ~12 hours, which serves to evaluate the thermal stability of the active layer. Subsequently, LiF and Al are thermally deposited under $10^{-6}$ Torr. In this device, ITO/PEDOT:PSS serves as the cathode while LiF/Al serves as the anode. Alternatively, after the active layer deposition, the active layer was dried in vacuo overnight. This was followed by thermal deposition of LiF/Al electrode, and the completed devices were then thermally treated at various temperatures, e.g. from room temperature to 90° C., for 10 min. The devices are measured in ambient conditions for PCE determination. A Newport Thermal Oriel 94021 1000 W solar simulator was used to generate a simulated AM 1.5 G solar spectrum irradiation source. The irradiation intensity was 100 mW cm$^{-2}$ calibrated by a standard silicon solar cell VS 0831.

(XV)

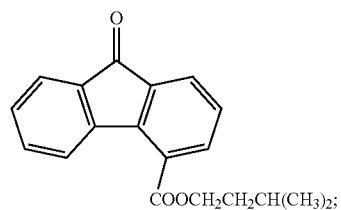

(XVI)

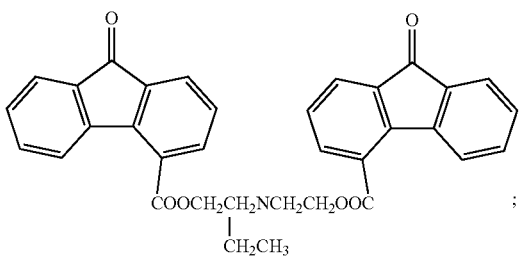

(XVII)

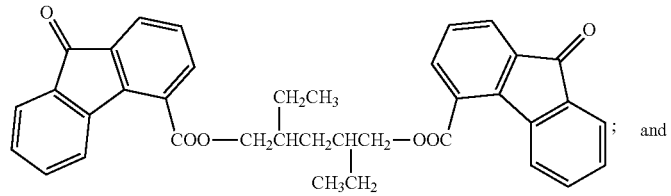

; and (XVIII)

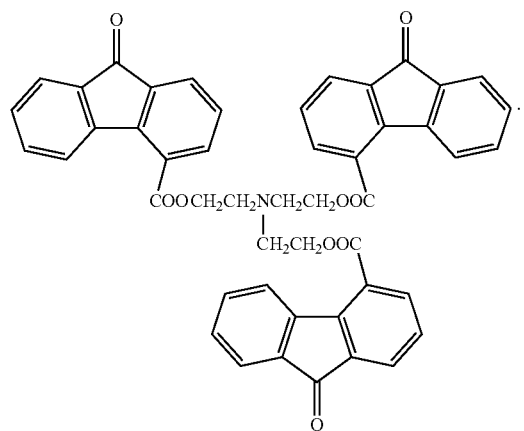

The effective amount of fluorenone derivative additive ranges from 0.01% to 5%, and preferably from 0.1% to 2% by weight, relative to the amount of electron donor polymer such as PTB7. The active layer materials (donor polymer, The following examples are provided to illustrate the invention, which by no means are exhaustive. They are intended to be illustrative only and are not intended to limit the scope of the invention.

Example 1

Synthesis of N,N,N-Tris(9-Dicyanomethylenefluorene-4-Carboxyethyl)Amine (XI)

(a) 4-Carboxy-9-florenylidene malononitrile: A mixture of 9.31 g (0.0415 mole) of fluorenone-4-carboxylic acid and 75 mL of absolute methanol was magnetically stirred and heated to reflux temperature in a round-bottomed flask fitted with a reflux condenser. Subsequently, there was added to the flask 8.23 g (0.125 mole) of malononitrile and 2 drops of piperidine. The mixture was then heated under reflux for 48 hours. The solid product 4-carboxy-9-fluorenylidene malononitrile, was collected by suction filtration, and purified by stirring in 50 mL of boiling methanol for 15 min, followed by filtration and washing successively with 20 mL of methanol. The product was dried under vacuum at 65° C. for 12 hours and weighed 9.01 g.

(b) 4-Chloroformyl-9-fluorenylidene malononitrile: A mixture of 2.74 grams (0.01 mole) of 4-carboxy-9-fluorenylidene malononitrile as obtained in (a) above, and 15 mL of thionyl chloride in a round-bottomed flask equipped with a reflux condenser was magnetically stirred and heated under reflux in a dry nitrogen atmosphere for 6 hours. The solid acid dissolved after 1 hour's heating. As the reaction proceeded, the reaction mixture turned brownish in color, and was a dark brown reaction mixture at the end of the reaction. The reaction mixture was then evaporated at reduced pressure resulting in a solid residue. Thereafter, 30 mL of dichloroethane was added to the mixture to dissolve the crude product. The resulting solution was then evaporated under reduced pressure to remove traces of thionyl chloride. The crude product was recrystallized from methylene chloride/hexane, and the pure 4-chloroformyl-9-fluorenylidene malononitrile obtained weighed 2.79 g after drying under a vacuum at 40° C. for 12 hours.

(c) To a gently stirred solution of 0.58 g (0.002 mol) 4-chloroformyl-9-fluorenylidenemalononitrile, 0.8 mL triethyl amine in 20 mL anhydrous methylene chloride in a round-bottomed flask cooled in an ice bath, a solution of 0.085 g triethanolamine in 1 mL methylene chloride was added slowly. The solution was stirred at room temperature overnight under $N_2$ atmosphere. At the end of the reaction, a saturated aqueous solution of $NaHCO_3$ was added. The organic layer was separated and the aqueous phase was extracted three times with dichloromethane. The combined organic layers were washed with brine, dried over $MgSO_4$, and upon solvent removal under reduced pressure, afforded a solid crude product. Purification by column chromatography through silica gel using dichloromethane as eluant gave 0.35 g of the pure product (XI).

(d) A series of comparative control devices with active layers treated at different temperatures were fabricated as follows: A solution of 5 mg of PTB7, 7.5 mg of PC70BM, and 15.6 µL of DIO in 500 µL chlorobenzene was spin-coated onto PEDOT:PSS coated ITO substrate. After coating, the active layer was dried or heated at an elevated temperature in an oven overnight (~12 hours). Subsequently, LiF and Al are thermally deposited on the active layer under $10^{-6}$ Torr. The device was then encapsulated in the glove box to complete the device fabrication. The performance (PCE) of the control devices with their active layers treated at various temperatures, e.g., from room temperature to 90° C., is shown in Table 1:

TABLE 1

Performance (PCE) of control devices with their active layers treated at various temperatures.

| Treatment Temp. (° C.) | PCE (%) |
| --- | --- |
| Room Temp | 7.8 |
| 40° C. | 7.1 |
| 70° C. | 6.2 |
| 90° C. | 5.3 |

Another series of sample devices with fluorenylidene malononitrile derivative (XI) additive were prepared in accordance with the procedure of control devices except that 0.04 mg of (XI) was added to the coating solutions. In this embodiment, the effective amount of fluorenylidene malononitrile additive used herein is 0.8% by weight, relative to the amount of electron donor polymer. The performance (PCE) of the sample devices with their active layers treated at various temperatures, e.g., from room temperature to 90° C., is shown at Table 2.

TABLE 2

Performance (PCE) of sample devices with their active layers treated at various temperatures.

| Treatment Temperature (° C.) | PCE (%) |
| --- | --- |
| Room Temp | 7.8 |
| 40° C. | 7.7 |
| 70° C. | 7.2 |
| 90° C. | 7.0 |

As can be noted, the PCE values of the sample devices with fluorenylidene malononitrile (XI) additive (Table 2) were superior to those of control devices without the additive (Table 1) at all temperatures. These results clearly show that the sample devices with fluorenylidene malononitrile (IX) additive were far more stable than the control devices.

Example 2

A series of control devices without fluorenylidene malononitrile additive were prepared in accordance with the procedure of EXAMPLE 1 except that after the active layer deposition, the active layer was dried in vacuo overnight. LiF/Al electrode was then deposited on the active layer, and the completed devices were then thermally treated at various temperatures, e.g., from room temperature to 90° C., for 10 min. The performance of control devices at various temperatures is shown in Table 3.

TABLE 3

Performance of control devices at various temperatures.

| Treatment Temperature | PCE (%) |
| --- | --- |
| Room Temp | 7.8 |
| 40° C. | 7.4 |
| 50° C. | 7.3 |
| 60° C. | 6.8 |
| 70° C. | 5.8 |

TABLE 3-continued

Performance of control devices at various temperatures.

| Treatment Temperature | PCE (%) |
|---|---|
| 80° C. | 5.1 |
| 90° C. | 4.8 |

Another series of sample devices with fluorenylidene malononitrile derivative (XI) were prepared in accordance with the above procedure for the control devices except that 0.04 mg of (XI) was added to the coating solutions. In this embodiment, the effective amount of fluorenylidene malononitrile additive used herein is 0.8% by weight, relative to the amount of electron donor polymer. The performance of sample devices at different temperatures, e.g., from room temperature to 90° C., is shown in Table 4.

TABLE 4

Performance of sample devices at various temperatures.

| Treatment Temperature | PCE (%) |
|---|---|
| Room Temp | 7.9 |
| 40° C. | 7.6 |
| 50° C. | 7.4 |
| 60° C. | 7.2 |
| 70° C. | 7.1 |
| 80° C. | 6.3 |
| 90° C. | 6.1 |

Again, the PCE values of the sample devices with fluorenylidene malononitrile (XI) additive (Table 4) were superior to those of control devices without fluorenylidene malononitrile additive (Table 3) at all treatment temperatures. These results clearly show that the sample devices with the additive were far more stable than control devices.

Example 3

Synthesis of 3,5-Bis(9-Dicyanomethylenefluorene-4-Carboxymethyl)Heptane (X)

To a gently stirred solution of 0.65 g (0.0022 mol) 4-chloroformyl-9-fluorenylidenemalononitrile, 0.5 mL triethylamine in 20 mL anhydrous methylene chloride in a round-bottomed flask cooled in an ice bath, a solution of 0.016 g 2,4-diethyl-1,5-pentanediol in 1 mL methylene chloride was added slowly. The solution was stirred at room temperature overnight under $N_2$ atmosphere. At the end of the reaction, a saturated aqueous solution of $NaHCO_3$ was added. The organic layer was separated and the aqueous phase was extracted three times with dichloromethane. The combined organic layers were washed with brine, dried over $MgSO_4$, and upon solvent removal under reduced pressure, afforded a solid crude product. Purification by column chromatography through silica gel using dichloromethane: hexane (2:1) as eluent gave 0.26 g of the pure product (X).

A series of sample devices with fluorenylidene malononitrile (X) additive as synthesized above were prepared in accordance with the procedure of EXAMPLE 1 (d) except that 0.04 mg of (X) was added to the coating solutions. In this embodiment, the effective amount of fluorenylidene malononitrile additive used herein is 0.8% by weight, relative to the amount of electron donor polymer. The PCE performance of sample devices with their active layers treated at various temperatures, e.g., from room temperature to 90° C., is shown at Table 5.

TABLE 5

Performance of sample devices with their active layers treated at various temperatures:

| Treatment Temperature (° C.) | PCE (%) |
|---|---|
| Room Temp | 7.9 |
| 40° C. | 7.8 |
| 70° C. | 7.6 |
| 90° C. | 7.3 |

As can be noted, the PCE values of these sample devices with fluorenylidene malononitrile (X) additive (Table 5) were superior to those of control devices (Table 1) without the additive at all treatment temperatures.

Example 4

Synthesis of [4-Iso-Pentoxycarbonyl-9-Fluorenylidene]Malononitrile (VIII)

A mixture of 9-fluorenone-4-carboxylic acid (1.0 g, 4.46 mmol), isopentyl alcohol (7.863 g, 89.2 mmol), conc. sulfuric acid (0.05 mL) and toluene (20 mL) in a 100-mL round-bottomed flask fitted with a Dean-stark apparatus and a water condenser was magnetically stirred and refluxed for 24 h before cooling to room temperature. After the reaction, the reaction mixture was evaporated under reduced pressure in the presence of $NaHCO_3$ (0.1 g). Subsequently, methylene chloride (100 mL) was added and the resulting solution was washed with dilute aq. $NaHCO_3$ solution (2 times) and with water (2 times), and dried with anhydrous $MgSO_4$. This was followed by filtration and evaporation under reduced pressure to give the crude product which was purified by flash chromatography on silica gel with hexane/ethyl acetate (volume ratio 15/1) as the eluent to afford iso-pentyl 9-fluorenone-4-carboxylate as a yellow oil (1.27 g, 97%).

A solution of isopentyl 9-fluorenone-4-carboxylate (1.2607 g, 4.28 mmol) as obtained above, malononitrile (0.8488 g, 12.85 mmol), and 1 drop of morpholine in 15 mL methanol was magnetically stirred and refluxed in a 50-mL round-bottomed flask for 24 h. After cooling to room temperature, the solid precipitate was filtered, washed twice with methanol, once with water, and dried in vacuo at 50° C. for 10 h. The crude product was recrystallized from acetone and methanol to yield [4-iso-pentoxycarbonyl-9-fluorenylidene]malononitrile (VIII) as an orange solid, m.p., 126~127° C. (1.31 g, 89.3%).

Photovoltaic Characterization

A series of sample devices with fluorenylidene malononitrile derivative (VIII) additive were prepared in accordance with the procedure of control devices of EXAMPLE 1 except that 0.04 mg of (VIII) was added to the coating solutions. In this embodiment, the effective amount of fluorenylidene malononitrile additive used herein is 0.8% by weight, relative to the amount of electron donor polymer. The performance of the sample devices with their active layers treated at various temperatures, e.g., from room temperature to 90° C., is shown at Table 6.

TABLE 6

Performance of sample devices with their active layers treated at various temperatures:

| Treatment Temperature | PCE (%) |
|---|---|
| Room Temp | 8.0 |
| 40° C. | 7.8 |
| 70° C. | 7.7 |
| 90° C. | 6.8 |

INDUSTRIAL APPLICABILITY

The present invention relates to the provision of an organic compound or compounds containing a fluorenone derivative structure or its substituted derivative to enhance the thermal stability of organic solar cells to prolong its useful life span.

What we claim:

1. An electron deficient compound used as an additive in an active layer in an organic solar cell wherein said electron deficient compound has a structure:

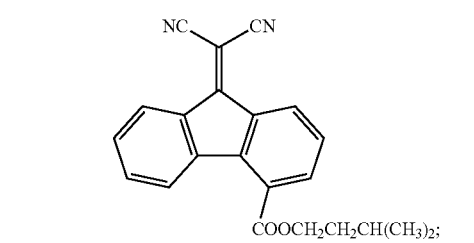
(VIII)

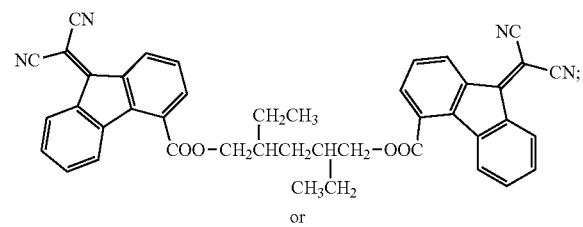
(X)

or

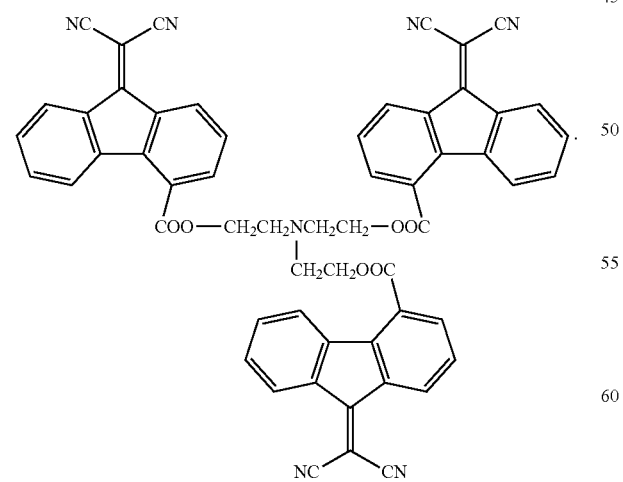
(XI)

2. An organic solar cell having at least one active layer comprising a PCBM acceptor, a donor polymer and a compound having a structure:

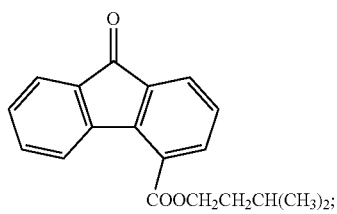
(XV)

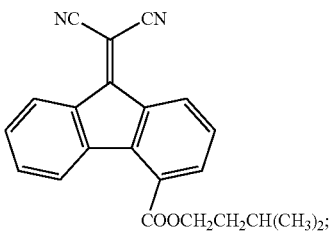
(VIII)

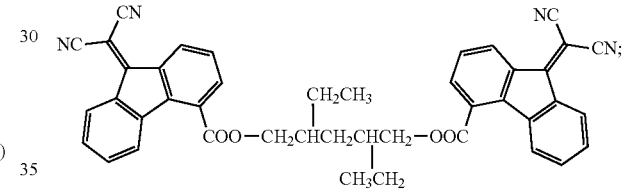
(X)

or

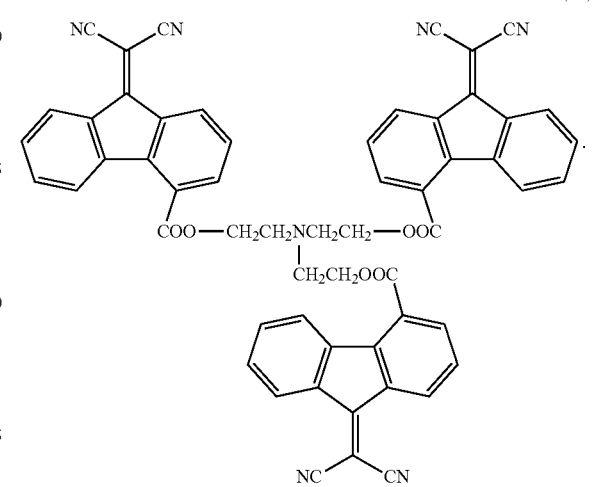
(XI)

3. The organic solar cell of claim 2, wherein the compound is present in an amount ranging from 0.01 to 5 percent by weight relative to the weight of the donor polymer in the at least one active layer of the organic solar cell.

* * * * *